United States Patent
Bernhardt et al.

(10) Patent No.: US 9,414,796 B2
(45) Date of Patent: Aug. 16, 2016

(54) X-RAY RECORDING SYSTEM FOR X-RAY IMAGING AT HIGH IMAGE FREQUENCIES OF AN OBJECT UNDER EXAMINATION BY WAY OF DIRECT MEASUREMENT OF THE INTERFERENCE PATTERN

(71) Applicant: SIEMENS AKTIENGESELLSCHAFT, Munich (DE)

(72) Inventors: Philipp Bernhardt, Forchheim (DE); Martin Spahn, Erlangen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 179 days.

(21) Appl. No.: 14/219,436

(22) Filed: Mar. 19, 2014

(65) Prior Publication Data
US 2014/0294148 A1    Oct. 2, 2014

(30) Foreign Application Priority Data
Mar. 27, 2013 (DE) .......................... 10 2013 205 406

(51) Int. Cl.
*A61B 6/00*  (2006.01)

(52) U.S. Cl.
CPC . *A61B 6/484* (2013.01); *A61B 6/42* (2013.01); *A61B 6/4208* (2013.01); *A61B 6/4233* (2013.01); *A61B 6/4441* (2013.01); *A61B 6/4458* (2013.01); *A61B 6/504* (2013.01)

(58) Field of Classification Search
CPC ............ A61B 6/03; A61B 6/032; A61B 6/42; A61B 6/4208; A61B 6/4233; A61B 6/4241; A61B 6/484

USPC .................. 378/19, 36, 62, 98.8; 250/370.09
See application file for complete search history.

(56) References Cited

U.S. PATENT DOCUMENTS

| 6,740,881 B2 | 5/2004 | Malmin |
| 6,847,042 B2 * | 1/2005 | Maolinbay .............. H01J 47/02 250/385.1 |

(Continued)

FOREIGN PATENT DOCUMENTS

| CN | 101257851 A | 9/2008 |
| CN | 101806912 A | 8/2010 |

(Continued)

OTHER PUBLICATIONS

Spahn, Martin et al., "Flat-panel detectors in X-ray systems", in: Der Radiologe, No. 5, vol. 43, 2003, pp. 340-350, DOI:10.1007/s00117-003-0890-y; DE; Abstract.

(Continued)

*Primary Examiner* — Allen C. Ho
(74) *Attorney, Agent, or Firm* — Harness, Dickey & Pierce, P.L.C.

(57) ABSTRACT

An x-ray recording system is disclosed for x-ray imaging of an object under examination by way of direct measurement of an interference pattern, especially for differential, real-time capable phase-contrast imaging. In at least one embodiment, the system includes with at least one x-ray emitter for creating quasi-coherent x-ray radiation; an x-ray image detector, including a detector layer and detector pixels arranged in a matrix; and a diffraction or phase grating, disposed between the object under examination and the x-ray image detector, configured to create an interference pattern, directly detectable in the nth Talbot order by an x-ray image detector with a very high achievable local resolution, which amounts to at least half the wavelength of the interference pattern in accordance with the Nyquist theory arising in the nth Talbot order.

18 Claims, 7 Drawing Sheets

(56) References Cited

U.S. PATENT DOCUMENTS

| | | | |
|---|---|---|---|
| 7,166,844 B1* | 1/2007 | Gormley | G01V 5/0016 250/358.1 |
| 7,253,416 B2* | 8/2007 | Fritzler | G01T 1/2928 250/370.1 |
| 7,433,443 B1* | 10/2008 | Tkaczyk | A61B 6/032 378/19 |
| 7,433,444 B2* | 10/2008 | Baumann | A61B 6/032 378/145 |
| 7,486,770 B2* | 2/2009 | Baumann | A61B 6/032 378/145 |
| 7,492,871 B2* | 2/2009 | Popescu | A61B 6/00 378/145 |
| 7,500,784 B2 | 3/2009 | Kemeth | |
| 7,522,698 B2* | 4/2009 | Popescu | A61B 6/032 378/19 |
| 7,522,708 B2* | 4/2009 | Heismann | A61B 6/00 378/145 |
| 7,532,704 B2* | 5/2009 | Hempel | A61B 6/032 378/145 |
| 7,535,986 B2* | 5/2009 | Hempel | A61B 5/02007 378/4 |
| 7,564,941 B2* | 7/2009 | Baumann | A61B 6/484 378/146 |
| 7,639,786 B2* | 12/2009 | Baumann | A61B 6/484 378/145 |
| 7,646,843 B2* | 1/2010 | Popescu | A61B 6/032 356/521 |
| 7,817,777 B2* | 10/2010 | Baumann | A61B 6/00 378/36 |
| 7,889,838 B2* | 2/2011 | David | A61B 6/4233 378/36 |
| 7,945,018 B2* | 5/2011 | Heismann | A61B 6/032 378/145 |
| 7,949,095 B2* | 5/2011 | Ning | A61B 6/032 378/4 |
| 7,983,381 B2* | 7/2011 | David | A61B 6/032 378/4 |
| 8,005,185 B2* | 8/2011 | Popescu | A61B 6/06 378/19 |
| 8,009,796 B2* | 8/2011 | Popescu | A61B 6/032 378/19 |
| 8,073,099 B2* | 12/2011 | Niu | A61B 6/00 378/36 |
| 8,094,776 B2* | 1/2012 | Takahashi | A61B 6/025 378/21 |
| 8,139,711 B2* | 3/2012 | Takahashi | A61B 6/00 356/457 |
| 8,165,270 B2* | 4/2012 | David | G01T 1/00 378/145 |
| 8,184,771 B2* | 5/2012 | Murakoshi | G01N 23/20075 378/145 |
| 8,223,924 B2* | 7/2012 | Borner | A61B 6/032 378/145 |
| 8,243,879 B2* | 8/2012 | Itoh | G21K 1/025 359/238 |
| 8,374,309 B2* | 2/2013 | Donath | A61B 6/032 378/145 |
| 8,451,975 B2* | 5/2013 | Tada | A61B 6/4291 378/207 |
| 8,591,108 B2* | 11/2013 | Tada | A61B 6/00 378/207 |
| 8,611,495 B2* | 12/2013 | Maschke | A61B 6/4014 378/197 |
| 8,632,247 B2* | 1/2014 | Ishii | A61B 6/00 378/207 |
| 8,755,487 B2* | 6/2014 | Kaneko | A61B 6/06 378/36 |
| 8,880,153 B2* | 11/2014 | Pfister | A61B 6/12 378/19 |
| 9,001,969 B2* | 4/2015 | Murakoshi | A61B 6/4233 378/70 |
| 9,179,883 B2* | 11/2015 | Spahn | A61B 6/484 |
| 2006/0054828 A1 | 3/2006 | Fritzler | |
| 2007/0183563 A1 | 8/2007 | Baumann | |
| 2009/0092227 A1 | 4/2009 | David et al. | |
| 2011/0274238 A1 | 11/2011 | Maschke | |
| 2011/0278463 A1 | 11/2011 | Miess et al. | |

FOREIGN PATENT DOCUMENTS

| | | |
|---|---|---|
| CN | 101011253 B | 6/2011 |
| CN | 102243317 A | 11/2011 |
| CN | 102288982 | 12/2011 |
| CN | 102871679 A | 1/2013 |
| DE | 102004043693 A1 | 3/2006 |
| DE | 102006037255 A1 | 8/2007 |
| DE | 102010018715 A1 | 11/2011 |
| DE | 102010019991 A1 | 11/2011 |
| JP | 2010154871 A | 7/2010 |

OTHER PUBLICATIONS

Martin Spahn, Volker Heer & Rudolf Freytag "Flachbilddetektoren in der Röntgendiagnostik", Der Radiologe, vol. 43 (2003), pp. 340-350; 2003; DE.

F. Pfeiffer et. al; Hard X-ray dark-field imaging using a grating interferometer Nature Materials, vol. 7, pp. 134-137; Feb. 1, 2008.

Martin Spahn, Flat detectors and their clinical applications Eur Radiol, vol. 15, pp. 1934-1947,; 2005; Apr. 2, 2005.

Joseph Zambelli, Nicholas Bevins, Zhihua Qi and Guang-Hong Chen; "Radiation dose efficiency comparison between differential phase contrast CT and conventional absorption CT"; Medical Physics, Jun. 2010, vol. 37, No. 6, pp. 2473-2479,; 2010.

German Office Action for German Application 10 2013 205 406.8 dated Oct. 14, 2013.

German Priority Document German Application 10 2013 205 406.8 filed Mar. 27, 2013.

Chinese Office Action and English translation thereof dated Oct. 29, 2015.

* cited by examiner

X-RAY RECORDING SYSTEM FOR X-RAY IMAGING AT HIGH IMAGE FREQUENCIES OF AN OBJECT UNDER EXAMINATION BY WAY OF DIRECT MEASUREMENT OF THE INTERFERENCE PATTERN

PRIORITY STATEMENT

The present application hereby claims priority under 35 U.S.C. §119 to German patent application number DE 102013205406.8 filed Mar. 27, 2013, the entire contents of which are hereby incorporated herein by reference.

FIELD

At least one embodiment of the invention generally relates to an x-ray recording system for x-ray imaging of an object under examination by way of direct measurement of an interference pattern, especially for differential real time-capable phase contrast imaging, with at least one x-ray emitter for generation of quasi-coherent x-ray radiation, an x-ray image detector, having a detector layer and detector pixels arranged in a matrix, a diffraction or phase grating which is disposed between the object under examination and the x-ray image detector and generates an interference pattern.

BACKGROUND

Differential phase-contrast imaging represents an imaging method which has attracted much attention for some time, especially in the Talbot-Lau interferometer arrangement. Thus for example the publication by F. Pfeiffer et al. [1], "Hard X-ray dark-field imaging using a grating interferometer", Nature Materials 7, 2008, Pages 134 to 137, describes how, with the aid of an interferometric structure, which includes a conventional x-ray tube, three gratings and an x-ray detector, both absorption contrast, differential phase contrast and also dark-field contrast can be reconstructed from the same dataset. Similar information can be found in Joseph J. Zambelli, et al. [2], "Radiation dose efficiency comparison between differential phase contrast CT and conventional absorption CT", Med. Phys. 37 (2010), Pages 2473 to 2479.

The wave nature of particles such as x-ray quanta allows the description of phenomena such as refraction and reflection with the aid of the complex refraction index $$n=1-\delta+i\beta.$$

In this case the imaginary part $\beta$ describes the absorption on which current clinical x-ray imaging, such as computed tomography, angiography, radiography, fluoroscopy or mammography is based, and the real part $\delta$ describes the phase offset, which is observed in differential phase imaging.

An x-ray recording system is known from DE 10 2010 018 715 A1 in which an x-ray recording system for phase-contrast imaging of an object under examination is used for high-quality x-ray imaging, having at least one x-ray emitter with a plurality of field emission x-ray sources for emitting a coherent x-ray radiation, an x-ray image detector, a diffraction grating $G_1$ disposed between the object under examination and the x-ray image detector and a further grating $G_2$, which is disposed between the diffraction grating $G_1$ and the x-ray image detector.

An x-ray recording system, which allows a differential phase-contrast imaging of the type stated at the start to be carried out, is known for example from U.S. Pat. No. 7,500,784 B2, which is explained with reference to FIG. 1.

FIG. 1 shows the typical main features of an x-ray recording system 1 for an interventional suite with a C-arm 2 held by a stand in the form of a six-axis industrial or articulated-arm robot, to the ends of which an x-ray radiation source, for example an x-ray emitter 3 with x-ray tube and collimator, and an x-ray image detector 4 as x-ray recording unit are attached.

By way of the articulated-arm robot known for example from U.S. Pat. No. 7,500,784 B2, which preferably has six axes of rotation and thereby six degrees of freedom, the C-arm 2 can be adjusted spatially in any given manner, for example by being rotated around a center of rotation between the x-ray emitter 3 and the x-ray image detector 4. The inventive x-ray recording system 1 is especially able to be rotated around centers of rotation and axes of rotation in the C-arm plane of the x-ray image detector 4, preferably around the center point of the x-ray image detector 4 and around the center point of axes of rotation intersecting with the x-ray image detector 4.

The known articulated-arm robot has a base stand, which is rigidly mounted on a floor for example. A carousel, able to be rotated around an axis of rotation, is fastened thereto. A robot rocker is attached to the carousel, pivotable around a second axis of rotation, to which a robot arm pivotable around a third axis of rotation is fastened. Attached to the end of the robot arm, pivotable around a forth axis of rotation is a robot hand. The robot hand has a fastening element for the C-arm 2, which is able to be pivoted around a fifth axis of rotation and able to be rotated around a sixth axis of rotation running at right angles thereto.

The realization of an x-ray recording system is not dependent on the industrial robots. Normal C-arm devices can also be used.

The x-ray image detector 4 can be a rectangular or square, flat x-ray detector, which preferably includes a scintillator (e.g. $C_sI$) and an active matrix of photodiodes made of amorphous Silicon (a-Si). However CMOS-based integrating detectors or also counting detectors (e.g. CdTe or CZT and ASIC) can also be used.

Located on a table plate 5 of a patient support table, in the beam path of the x-ray emitter 3, as the object under examination, is a patient 6 to be examined. Connected to the x-ray recording system 1 is a system control unit 7 with an imaging system 8, which receives the image signals of the x-ray image detector 4 and processes them (operating elements are not shown for example). The x-ray images can then be viewed on displays of a monitor array 9. The monitor array 9 can be held by way of a ceiling-mounted, longitudinally-movable, pivot, rotation and height-adjustable support system 10 with outriggers and a lowerable support arm.

Instead of the x-ray recording system 1 with the stand in the form of the six-axis industrial or articulated-arm robot as shown by way of example in FIG. 1 the x-ray recording system 1 can, as shown in FIG. 2 in simplified form also have a normal ceiling-mounted or floor-mounted holder for the C-arm 2.

Instead of the C-arm 2 shown by way of example, the x-ray recording system 1 can also have separate ceiling-mounted and/or floor-mounted holders for the x-ray emitter 3 and the x-ray image detector 4, which are electronically rigidly coupled for example.

In the current arrangements focused on for clinical phase-contrast imaging conventional x-ray tubes, currently available x-ray image detectors, such as are described for a example by Martin Spahn [3] in "Flat detectors and their clinical applications", European Radiology, Volume 15 (2005), Pages 1934 to 1947, and three gratings $G_0$, $G_1$ and $G_2$ are used, as is explained below with reference to FIG. 2, which shows a schematic structure of a Talbot-Lau interferometer for differential phase-contrast imaging with the extended tube focus, gratings $G_0$, $G_1$ and $G_2$ and pixelated x-ray image detector.

The x-ray beams 12 emerging from a tube focus 11 of the non-coherent x-ray emitter 3, for generation of coherent radiation, penetrate an absorption grating 13 ($G_0$), which brings about the local coherence of the x-ray emitter 3, and also an object under examination 14, for example the patient 6. Through the object under examination 14 the wave front of the x-ray beams 12 is deflected by phase offsetting in such a way as illustrated by the normal 15 of the wave front without phase offsetting, i.e. without object, and the normal 16 of the wave front with phase offsetting. Subsequently the phase-offset wavefront passes through a diffraction or phase grating 17 ($G_1$) with a grating constant adapted to the typical energy of the x-ray spectrum for generation of interference lines or an interference pattern 18 and in its turn an absorbing analyzer grating 19 ($G_2$) for reading out the interference pattern 18 generated. Different interference patterns 18 arise with and without object. The grating constant of the absorbing analyzer grating 19 is adapted to that of the phase grating 17 and the remaining geometry of the arrangement. The absorbing analyzer grating 19 is disposed for example in the first or nth Talbot spacing (order). The absorbing analyzer grating 19 in this case converts the interference pattern 18 into an intensity pattern, which can be measured by the x-ray image detector 4. Typical grating constants for clinical applications lie at a few μm, as can also be found in the cited literature references [1, 2].

If the x-ray emitter 3 is sufficiently coherent, i.e. the tube focus 11 of the x-ray emitter 3 is sufficiently small and the generated radiation power is still sufficiently large, it is possible to dispense with the first grating $G_0$, the absorption grating 13.

The differential phase offsetting is now determined for each pixel of the x-ray image detector 4 according to the prior art by, through what is referred to as "phase stepping" 20, which is indicated by an arrow, the absorbing analyzer grating 19 ($G_2$), being displaced in a number of steps (k=1, K, with e.g. K=4 to 8) by a corresponding fraction of the grating constant at right angles to the radiation direction of the x-ray beams 12 and lateral to the arrangement of the grating structure and by, for this configuration, the signal $S_k$ arising during the imaging in the pixel of the x-ray image detector 4 being measured and the interference pattern 18 produced being sampled. For each pixel the parameters of a function describing the modulation (e.g. sine) are then determined by a suitable fit method, an adaptation or compensation method, to the signals $S_k$ thus measured. These parameters are usually the amplitude A, the phase $\Phi$ and the average intensity I.

The comparison of specific derived variables from these fit parameters for each pixel, once with and once without object (or patient), then enables three different images to be created:

Absorption image,

Differential phase-contrast (DPC) image and

Dark-field image.

The visibility, i.e. the standardized difference between the maximum and minimum signal (or more precisely: amplitude standardized to the average signal) is in this case a measure for characterizing the quality of a Talbot-Lau interferometer. It is defined as the contrast of the sampled modulation $$V = \frac{I_{max} - I_{min}}{I_{max} + I_{min}} = \frac{A}{I}$$

References in this document to an image may possibly mean the triumvirate of absorption image, DPC image and dark field image.

The realization of the method presents many challenges, but in particular has two decisive disadvantages:

The absorbing analyzer grating $G_2$ must be moved into different positions and then an x-ray acquisition carried out in each position. Such a method is thus conceivably unsuitable for moving objects (such as non-anaesthetized patients or patient organs, e.g. heart, lungs) if the object moves between the different measurements even by small distances. Likewise such an arrangement is unsuitable on account of the mechanical movement of the absorbing analyzer grating $G_2$, in order to make possible real-time imaging or imaging at higher image frequencies of for example 15 images per second (I/s) or also 60 to 100 I/s. 3D imaging, in which x-ray tube and x-ray detector are rotated continuously around the patient, are also not possible in this way.

The fact that the absorbing analyzer grating $G_2$ is an analyzer grating with areas in which it is transparent for x-rays and in other areas is as non-transparent as possible means that dose (typically 50%) is lost behind the object or the patient, which is not effective in the image.

SUMMARY

At least one embodiment of the invention embodies an x-ray recording system in which a real time-capable phase-contrast imaging at high image frequencies is made possible, wherein the x-ray image detector has a structure which does not provide for any analyzer grating $G_2$ or for any mechanical movement of the x-ray image detector.

At least one embodiment of the invention is directed to an x-ray recording system. Advantageous embodiments are specified in the dependent claims.

At least one embodiment of the invention is directed to an x-ray recording system by the interference pattern in the nth Talbot order (with and without object) being detected directly by an x-ray image detector with a very high achievable local resolution, which amounts to at least half the wavelength of the interference pattern arising in the nth Talbot order in accordance with the Nyquist theory.

In accordance with at least one embodiment of the invention, the suitable function can be a fit function and/or a weighted averaging in accordance with the equation $(X,Y)=\Sigma (x_i, y_i) \cdot S_i / \Sigma S_i$, wherein $(X,Y)$ is the computed location, $(x_i, y_i)$ e.g. the center points of the detector pixels (22) involved in the averaging and $S_i$ the measured pixel signals 26 in the corresponding pixels i.

BRIEF DESCRIPTION OF THE DRAWINGS

The invention is explained in greater detail below with reference to the example embodiments shown in the drawing. In the figures.

DETAILED DESCRIPTION OF THE EXAMPLE EMBODIMENTS

Figure 1:
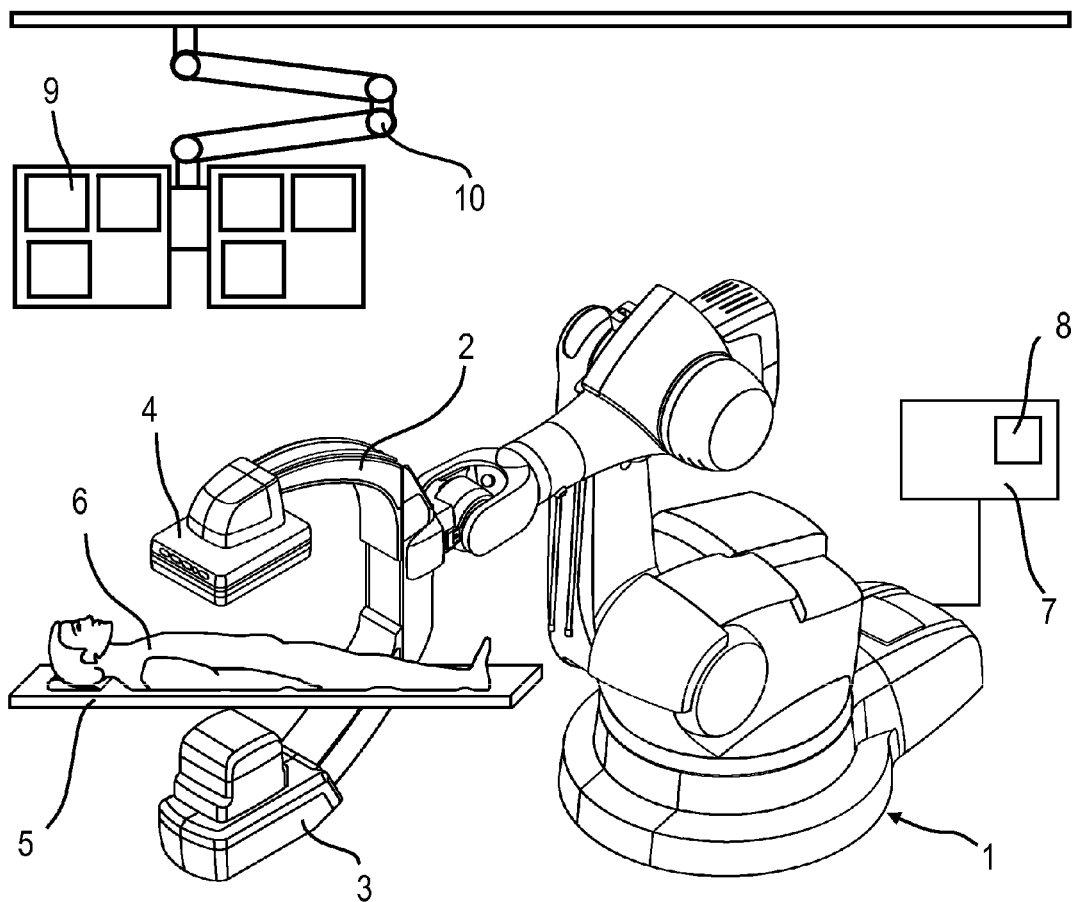
FIG. 1 shows a known C-arm angiography system of an interventional suite with an industrial robot as support apparatus.
Figure 2:
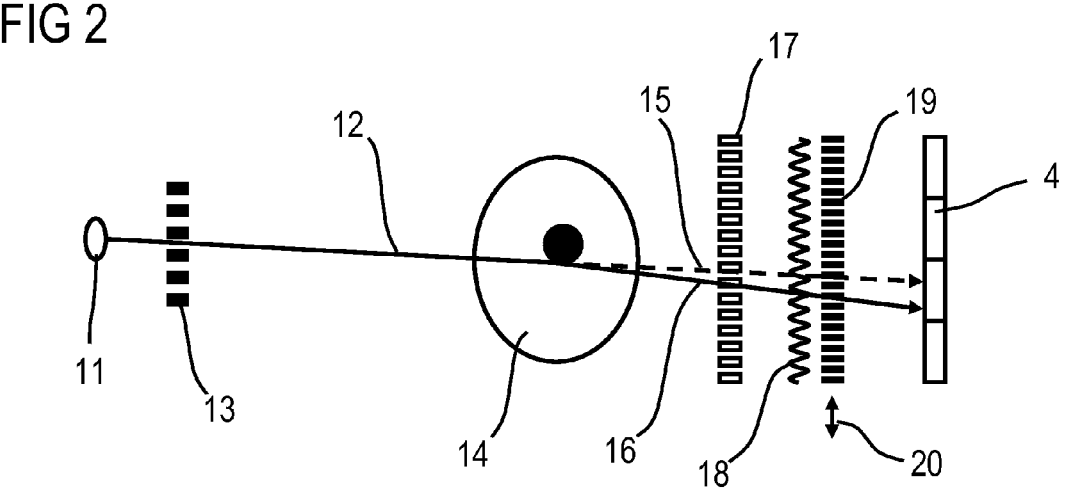
FIG. 2 shows a schematic layout of a known Talbot-Lau interferometer for differential phase-contrast imaging with extended tube focus, three gratings $G_0$, $G_1$ and $G_2$ and pixelated detector.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

At least one embodiment of the invention is directed to an x-ray recording system by the interference pattern in the nth Talbot order (with and without object) being detected directly by an x-ray image detector 4 with a very high achievable local resolution, which amounts to at least half the wavelength of the interference pattern arising in the nth Talbot order in accordance with the Nyquist theory.

This achieves the result that a real time-capable phase-contrast imaging is possible at a high image frequency. Neither an analyzer grating $G_2$ nor a mechanical movement of the x-ray image detector 4 is required for phase-contrast imaging. The local resolution can also be higher than that of the half wavelength of the interference pattern 18. In precise terms the x-ray spectrum naturally also creates a spectrum of interference patterns of different wavelengths. What is meant here is the "design wavelength" of the structure which is optimized for the interference pattern of a specific x-ray energy, for example 50, 70 or 90 keV, arising.

In accordance with at least one embodiment of the invention the x-ray imaging can create an absorption image, a differential phase-contrast (DPC) image or a dark field image.

It has proved advantageous for the x-ray emitter 3 for generation of quasi-coherent x-ray radiation, to use an x-ray tube usually used in x-ray diagnostics or angiography with a relatively large tube focus 11 and for the coherence to be created by the use of an absorption grating $G_0$.

In an advantageous manner, the x-ray emitter 3 for creation of quasi-coherent x-ray radiation can as an alternative have a plurality of field emission x-ray sources of sufficiently small focus sizes or a sufficiently powerful micro focus source. In this case no absorption grating $G_0$ is necessary.

Figure 3:
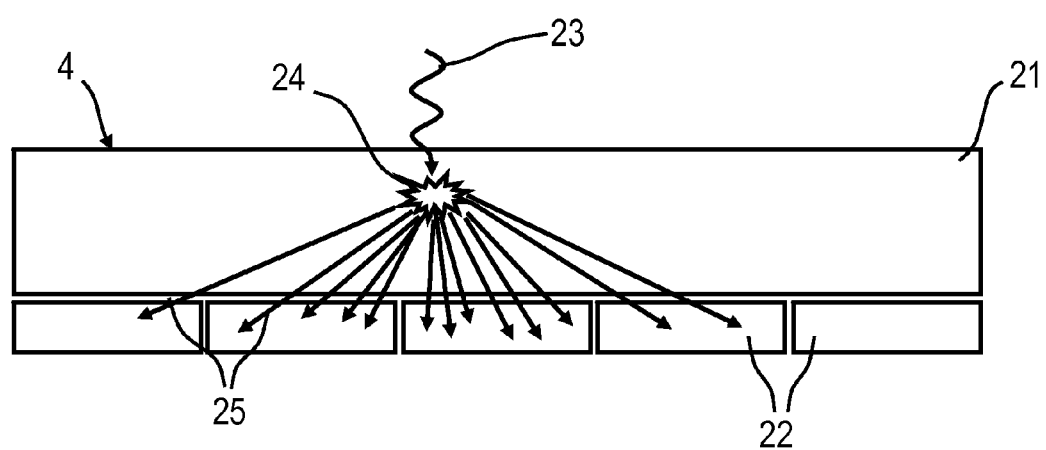
FIG. 3 shows a schematic diagram of a detector structure in a side view with a detector layer and light-sensitive detector pixels.
Figure 4:
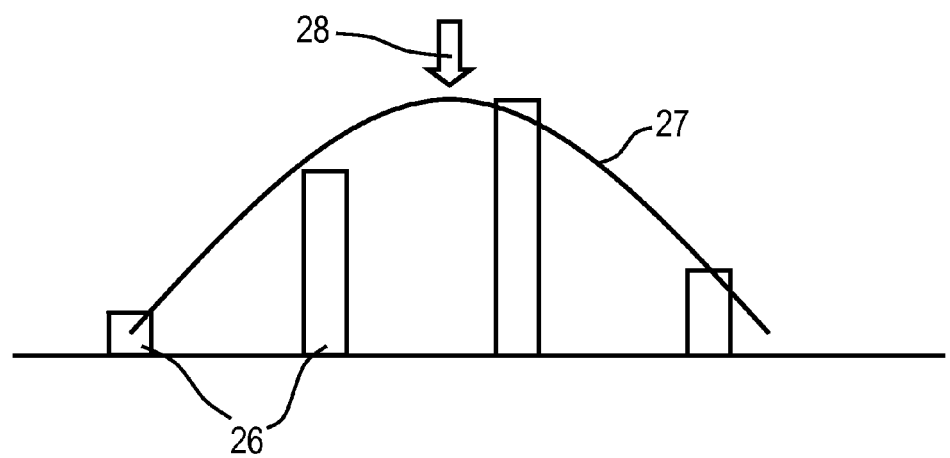
FIG. 4 shows an example distribution of the output signals of the detector pixels according to FIG. 3.

With reference to FIGS. 3-4, the very high local resolution of the x-ray image detector (4) is achieved if the detector pixel (22) of the x-ray image detector (4) has pixel sizes, of which the surfaces are significantly larger than the surfaces actually required for the resolution to be achieved, the detector layer (21) includes the detector material, which creates many secondary quanta (25) for each absorbed x-ray quantum (23) and has such an inherently "bad" modulation transfer function (MTF) that the secondary quanta (25) occurred distributed over at least two detector pixels (22) and detected there as pixel signals (26), and the location of the primary event (24) is reconstructed via measured pixel signals (26) in a number of pixels (32, 34).

Significantly more precisely than would be expected from the size of the detector pixels 22, the location of the primary event 24 can be determined if it is determined with the aid of a suitable function via the pixel signals 26 measured in the neighboring pixels.

In accordance with at least one embodiment of the invention, the suitable function can be a fit function and/or a weighted averaging in accordance with the equation $(X,Y)=\Sigma(x_i, y_i) \cdot S_i / \Sigma S_i$, wherein $(X,Y)$ is the computed location, $(x_i, y_i)$ e.g. the center points of the detector pixels (22) involved in the averaging and $S_i$ the measured pixel signals 26 in the corresponding pixels i.

In an advantageous manner the detector pixels 22 can be connected via pixel-to-pixel connections to at least the directly neighboring pixels and possibly the neighboring pixels after next.

It has proved advantageous for the reconstruction of the location of the primary event 24 to be undertaken directly in the pixel matrix and for each primary event 24 of the calculated location to be retained.

Processing can take place outside the x-ray image detector 4 if the signal levels of the pixel signals 26 of all pixels involved in these primary events 24 and a time stamp are retained and the reconstruction is undertaken later, wherein the detector pixels 22 involved are able to be allocated subsequently via the time stamp.

In an advantageous manner the detector layer 21 can include a scintillator material, in which the created secondary quanta 25, the light photons, are distributed over a number of detector pixels 22, wherein the speed of the scintillator material must be selected as a function of the level of the x-ray flow to be expected, so that no time constants are produced, wherein it is true to say that the higher the x-ray flow is, the "faster" the detector material must be.

It has proved to be advantageous for the x-ray image detector 4 to be an integrating detector with indirect conversion of the x-ray quanta by way of CsI as scintillator material and amorphous silicon or CMOS for the photodiode and readout structure or to be implemented as a photon counting detector with direct conversion of the x-ray quanta.

A section of the x-ray image detector 4 is shown schematically (cross-section) in FIG. 3 with a detector layer 21 made of a conversion material and a layer lying therebelow with light-sensitive detector pixels 22. An x-ray quantum 23 strikes the x-ray image detector 4 and creates a primary event 24 as a result of the absorption of the x-ray quantum 23 in the excited luminescent material of the detector layer 21, through which secondary quanta 25 are emitted. These emitted secondary quanta 25 will be detected by the light-sensitive detector pixels 22.

FIG. 4 now shows the possible distribution of the output signals according to FIG. 3 as pixel signals 26, which can be analog voltages or digital numerical values over which a fit function 27 has been laid as adaptation, which is a mathematical optimization method to determine or to estimate the unknown parameters of a model or of a predetermined function for a series of measurement data. The maximum 28 of the fit function 27 produces a virtual location or reconstructed location. In the ideal case the positions of the primary event 24 and the maximum 28 of the fit function 27 are identical.

Figure 5:
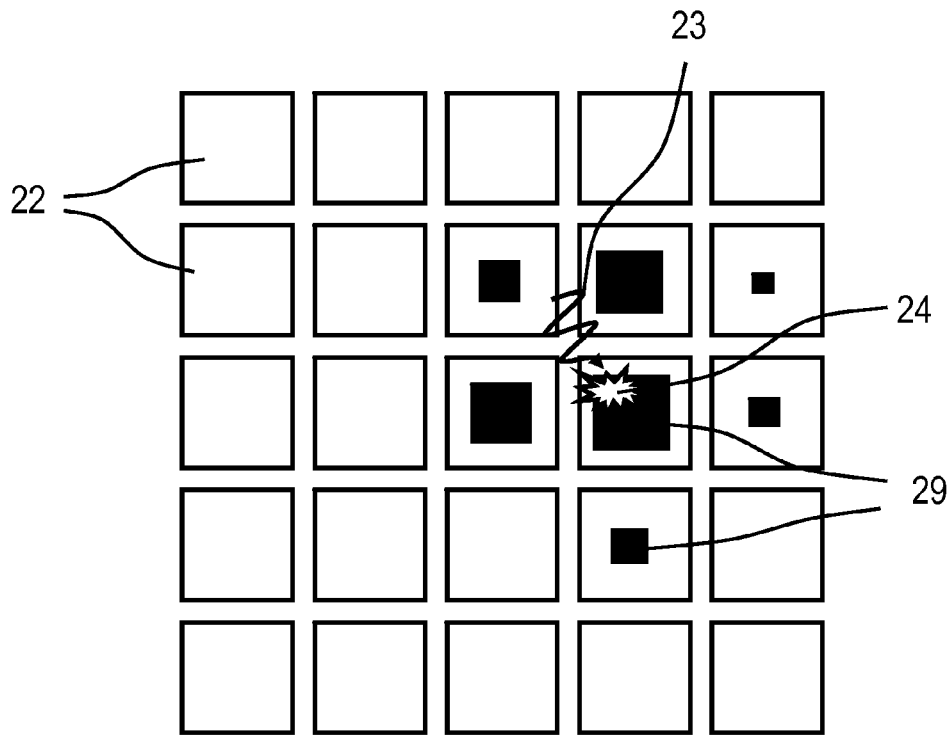
FIG. 5 shows the detector arrangement according to FIG. 3, viewed from above with interaction of an x-ray quantum.

The detector arrangement in accordance with FIG. 3 is shown in FIG. 5 in an overhead view with the x-ray quantum 23 striking the x-ray image detector 4, which creates the primary event 24. The emitted secondary quanta 25 (not shown) fall on differently strongly excited adjacent detector pixels 29, wherein the different distribution of the pixel signals 26 is indicated schematically by squares of different sizes.

Now, from this distribution, as is illustrated with reference to FIG. 6, the virtual location 31 of the primary event 24 at which the x-ray quantum 23 has interacted with the detector material, is determined by way of suitable two-dimensional fit functions 30, which are drawn-in here in the shape of circles.

It is now shown schematically, with reference to FIGS. 7 to 12, how the detector pixels 22 of the x-ray image detector 4, shown viewed from above for determining the distribution of the pixel signals 26, can be connected to one another.

Figure 7:
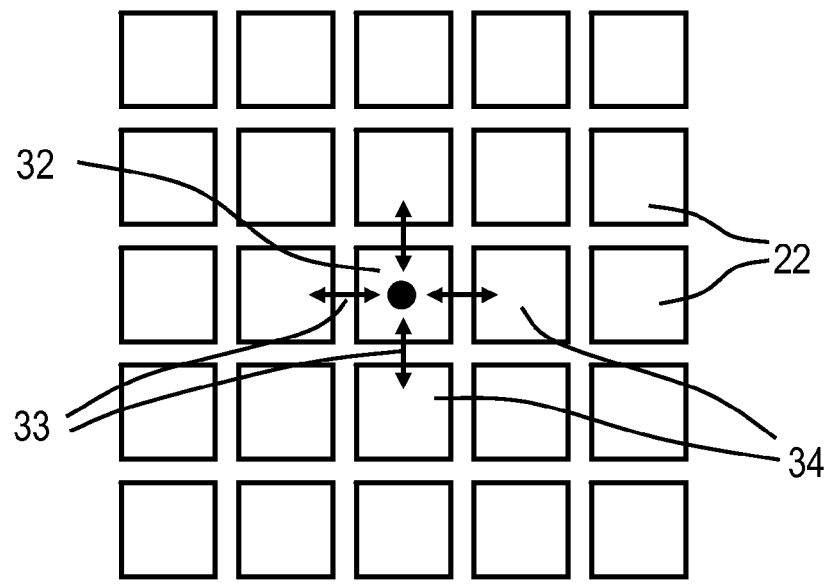
FIGS. 7 to 12 show various examples of possibilities of pixel-to-pixel connections.

Referring to FIG. 7, a central pixel 32 is connected via pixel-to-pixel connections 33 with the respective horizontal and vertical directly-neighboring pixels 34. Thus five detector pixels 22 are grouped together in this arrangement.

Figure 8:
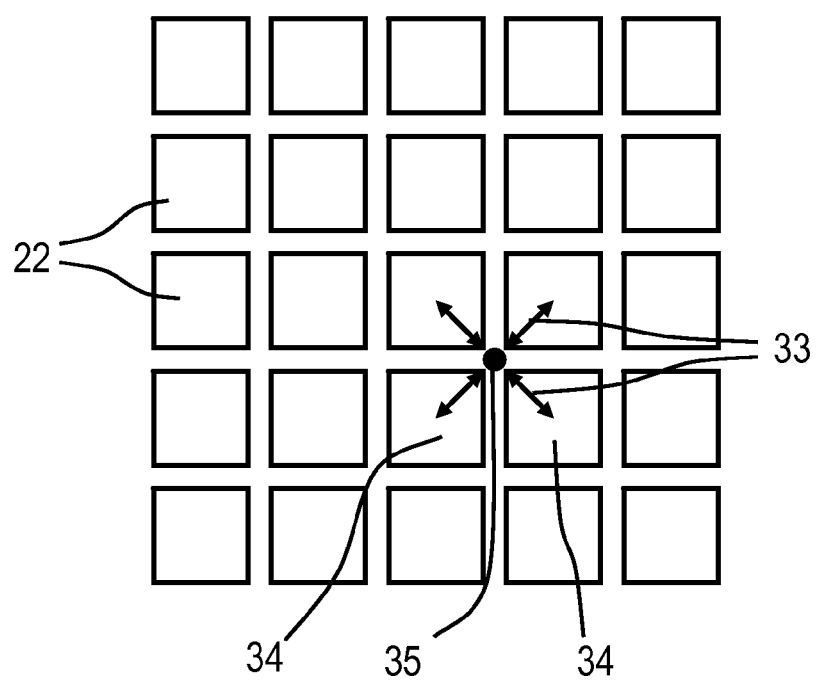

A node 35 lying between the detector pixels 22 is connected according to FIG. 8 via pixel-to-pixel connections 33 diagonally to directly-neighboring pixels 34, so that four detector pixels 22 are grouped together.

Figure 9:
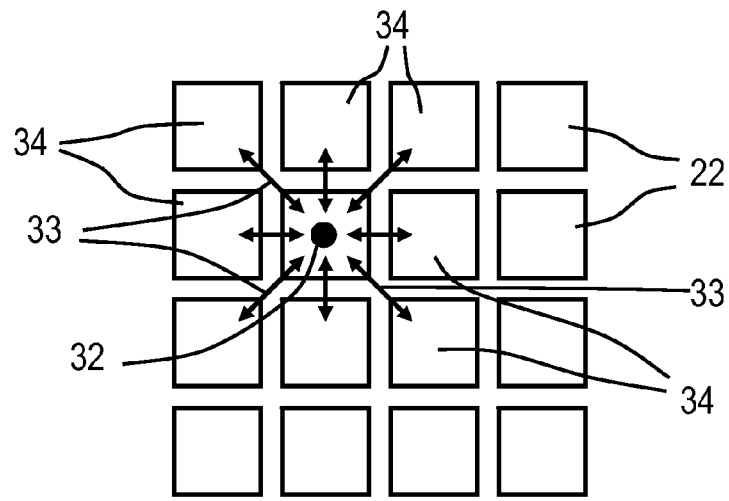

FIG. 9 shows a version in which, radiating from the central pixel 32, via pixel-to-pixel connections 33, the respective horizontally and vertically and also diagonally directly-neighboring pixels 34 are connected. This allows the pixel signals 26 of nine detector pixels 22 to be grouped together.

Figure 10:
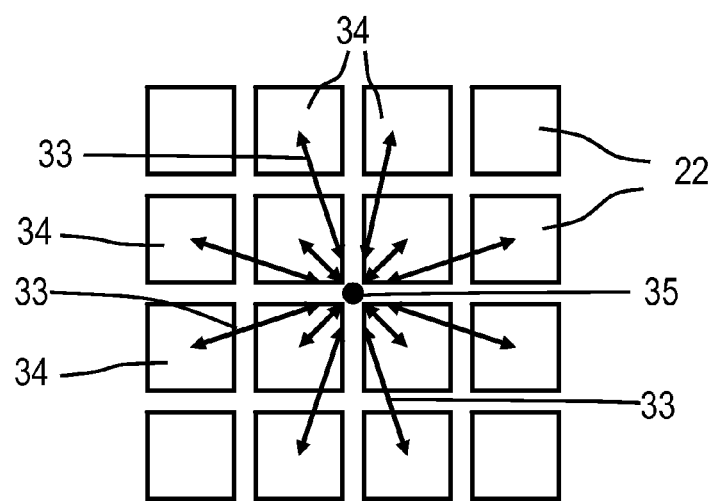

The arrangement according to FIG. 10 makes it possible for the pixel signals 26 of the diagonal directly-neighboring pixels 34 and their respective horizontal and vertical directly-neighboring pixels 34 to be detected by a node 35 lying between the detector pixels 22 via pixel-to-pixel connections 33, so that a total of 12 detector pixels 22 will be evaluated.

Figure 11:
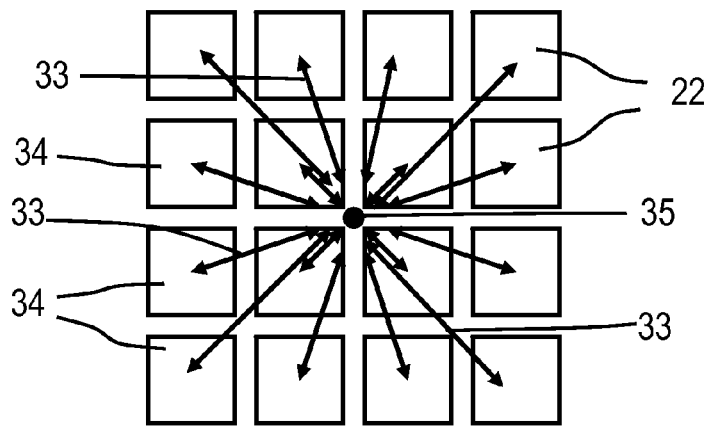

In the example according to FIG. 11, starting from the arrangement of FIG. 10, the next diagonal neighboring pixels 34 will also be detected so that now a total of 16 detector pixels 22 contribute to the evaluation.

Figure 12:
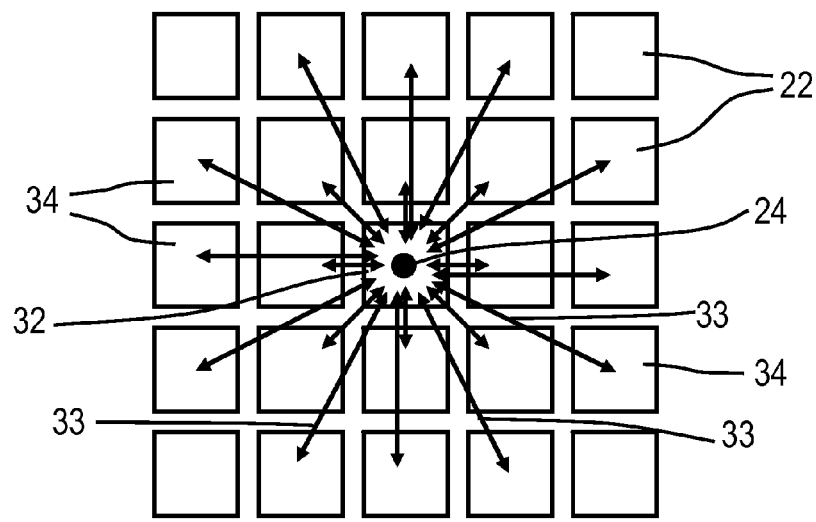

FIG. 12 shows a structure in which, starting from central pixel 32 with the primary event 24, the respective horizontal and vertical direct and next neighboring pixels 34 as well is the diagonal directly-neighboring pixels 34 and their respective horizontal and vertical directly-neighboring pixels 34 are connected by way of pixel-to-pixel connections 33. This allows the pixel signals 26 from twenty one detector pixels 22 to be grouped together. If the diagonal next neighboring pixels 34 are also included, twenty five detector pixels 22 can be evaluated.

Figure 13:
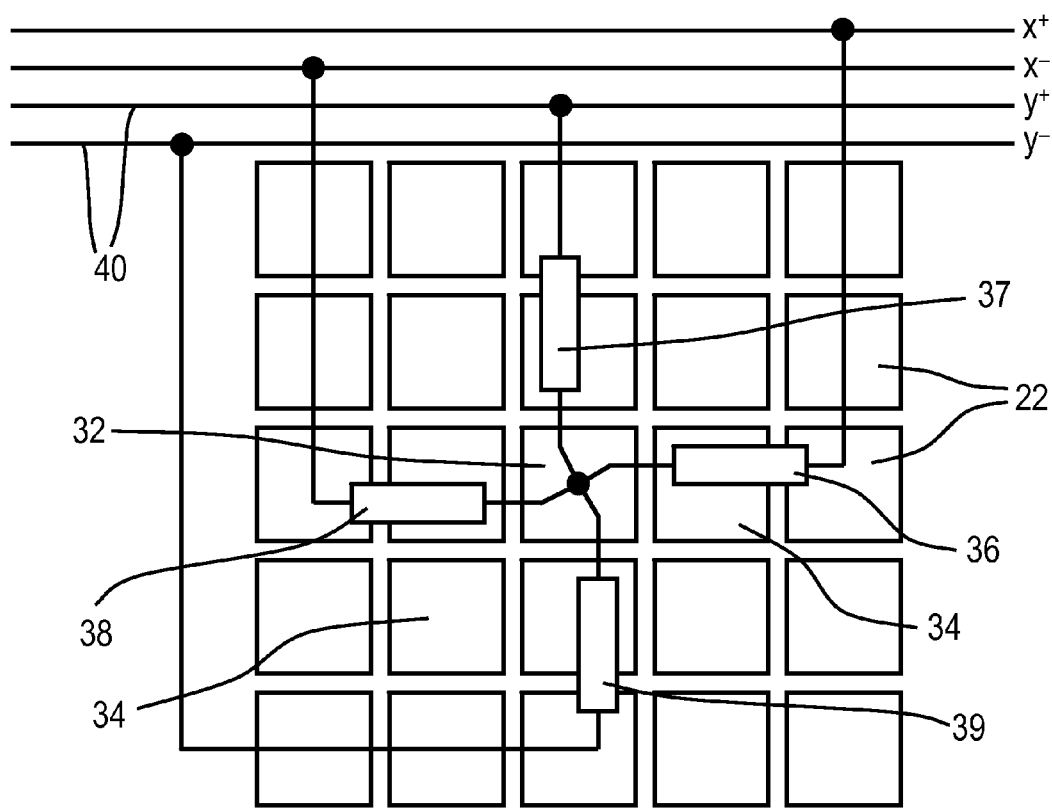
FIG. 13 shows a section of a resistance network for analog evaluation of a number of detector pixels.

A common analog evaluation of a number of detector pixels 22 can for example be achieved by a resistance network, which is shown in FIG. 13 in cross-section only for the central pixel 32. The resistance network has the resistor 36 ($R(x^+)$), resistor 37 ($R(y^+)$), resistor 38 ($R(x^-)$), and resistor 39 ($R(y^-)$), which are connected to connecting lines 40 ($x^+$, $x^-$, $y^+$, $y^-$), via which the pixel signals 26 can be tapped off. With a suitable choice of resistors 36 to 39 and those of the neighboring pixels 34 a significantly higher local resolution than the pixel resolution can be achieved.

Figure 14:
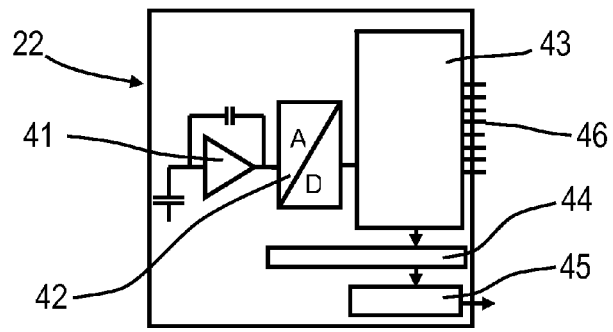
FIG. 14 shows the circuit-technology structure of an embodiment of the inventive detector pixel.

FIG. 14 now shows a schematic of the layout of a detector pixel 22. The input signal of the light-sensitive element of the detector pixel 22 is supplied to an amplifier 41, the output signal of which is digitized in an analog/digital converter (A/D converter) 42, so that it is processed by a computation unit 43 and buffered in a memory 44 for further evaluation. The results are fed as an image signal via readout electronics 45 or readout logic to the imaging system 8. Via connections 46 the detector pixels 22 are connected to one another for joint evaluation of their pixel signals 26, as has been described with reference to the examples according to FIGS. 7 to 12.

By way of this memory 44 the signal levels of the pixel signals 26 of all pixels 32 and 34 involved in these primary events 24 and a time stamp can be maintained. The reconstruction can take place later for example outside the x-ray image detector 4, by the pixel signals 26 of the detector pixels 22 involved being able to be allocated afterwards via the time stamp.

Figure 15:
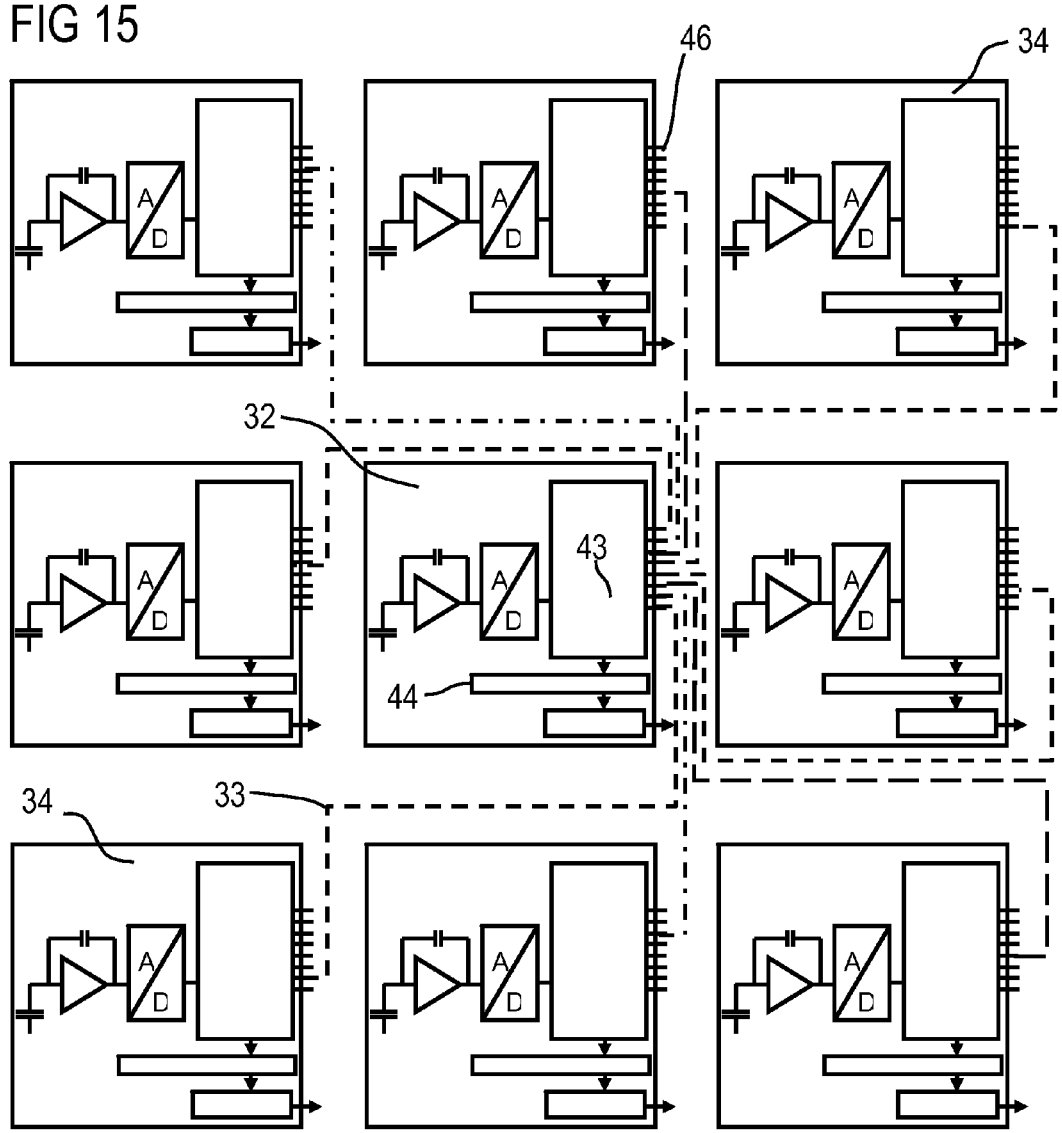
FIG. 15 shows a circuit technology implementation of a central detector pixel with a number of neighboring detector pixels.

According to FIG. 15 nine such detector pixels 22 are connected to one another. Starting from the connections 46 of the central pixel 32, all pixel-to-pixel connections 33 go to the connections 46 of the eight neighboring pixels 34. From these digital pixel signals 26, by way of the computation unit 43 on the basis of a signal weighting (according to the equation (1)) or the two-dimensional fit functions 30 to the signal values, the maximum of the two dimensional fit function 30 is determined and thus a virtual location is established and a precise location signal calculated, which is stored, together with the level of the overall signal in memory 44. The two location determinations described using the simple-to-implement signal weighting in accordance with equation (1) or a significantly more complex fit of a two dimensional fit function 30 are alternatives.

Advantages produced by at least one embodiment of the inventive structure of the x-ray image detector 4 for real time-capable phase-contrast imaging at high image frequencies through direct measurement of the interference pattern 18 include the following:

with this structure no mechanical movements will be needed, since the intensity distribution in the nth Talbot order is measured directly with the x-ray image detector 4, so that no absorbing analyzer grating $G_2$ and no phase stepping are needed, it makes possible real-time imaging and the dose loss through absorbing analyzer grating $G_2$ behind the patient—a significant disadvantage of the Talbot-Lau method with absorbing analyzer grating $G_2$ and phase stepping—does not arise here since with the realization described, this is not needed.

The inventive method of at least one embodiment described here is based on the interference pattern 18 in the nth Talbot order (with and without object) being measured directly by a suitable x-ray image detector 4. For this purpose however a very high local resolution is needed. An x-ray image detector 4 having a resolution of at least half the wavelength of the interference pattern 18 in accordance with the Nyquist Theorem arising in the nth Talbot order, is realized as follows:

pixel sizes can be used in the x-ray image detector 4, the surfaces of which are significantly larger than the surfaces actually required for the resolution to be achieved.

a detector material is used which for each absorbed x-ray photon creates many secondary quanta 25 and has an inherently "bad" MTF (Modulation transfer function), so that the secondary quanta 25 are distributed over at least two—as a rule significantly more—detector pixels 22 and are detected there has pixel signals 26 (e.g. scintillator material would be suitable here in which the created light photons are distributed over a number of detector pixels 22. It is true to say here that the higher the x-ray flow to be expected is, the "faster" the detector material must be—small time constants).

the location of the x-ray absorption event, of the primary event 24 is reconstructed by the measured pixel signals 26 in the adjacent pixels, the neighboring pixels 34. The absorption location of the x-ray quantum 23 can be determined significantly more precisely via the pixel signals 26 measured in the neighboring pixels 34 with the aid of a suitable function, for example the fit function 27, than would be expected from the size of the detector pixels 22.

a connection of the pixels is necessary, at least of the directly-neighboring pixels 34 possibly the neighboring pixels 34 after next, etc. The reconstruction can for example be undertaken directly in the pixel matrix and for each event the computed location (x, y) can be recorded or the signal levels of all pixels involved in this primary event 24 and a time stamp can be recorded and the reconstruction can take place later, e.g. outside the x-ray image detector 4, by the detector pixels 22 involved being able to be allocated subsequently via the time stamp. Further options are conceivable so that these cited examples are not restrictive.

A simple signal-weighted averaging over the locations at which the primary events 24, the absorption of the x-ray quantum 23, has been verified is suitable for example as a function for improving the local resolution:

$$(X,Y) = \Sigma(x_i, y_i) \cdot S_i / \Sigma S_i \qquad (1)$$

(X, Y) is the calculated (average) location, $(x_i, y_i)$ e.g. the center points of the detector pixels 22 involved in the averaging and $S_i$ the measured pixel signals 26 in the corresponding pixels i. The sum is formed over all pixels i of the neighborhood (as shown for example in FIGS. 7 to 12).

In such cases the detector pixels 22 are either placed around a central pixel 32 (examples in FIGS. 7, 9 and 12) or also around a node 35 lying between detector pixels 22 (examples in FIGS. 8, 10 and 11).

In principle such an averaging method can be carried out in the analog or in the digital "space".

In the analog space the analog pixel signals 26 are present in accordance with the energy deposited in the corresponding detector pixels 22. The location can be determined by a network of resistors 36 to 39, which are arranged connected between the detector pixels 22:

$$X = c \cdot \Sigma(x^+ - x^-), Y = c \cdot \Sigma(y^+ - y^-) \qquad (2)$$

wherein
c is a suitable constant.

The values $x^+$, $x^-$, $y^+$, $y^-$ are formed from those detector pixels 22 which are formed in the resistance network 36 to 39 in the area of a central pixel 32 or of a node 35 lying between detector pixels 22 (see also FIG. 13).

If the pixel signals 26 are available digitally, i.e. after amplification and conversion of the analog signal in the corresponding detector pixels 22 with a sufficiently resolving analog-to-digital converter (ADC) 42 for example, the location can be computed by way of the equation (1) for a digital networking between the corresponding detector pixels 22 (as indicated in the FIGS. 7 to 12).

The architecture of such detector pixels 22 and the connection with the neighboring pixels 34 is shown by way of example in FIG. 15, where each detector pixel 22 is linked to its eight directly-neighboring pixels 34 (this corresponds to the case depicted in FIG. 9). A section from a pixel matrix is shown in FIG. 15, with connection of a central pixel 32 to its eight neighboring pixels 34. A precise location signal is computed by signal weighting from the digital pixel signal 26 of the central pixel 32 and its eight neighboring pixels 34, which is stored, together with the level of the overall signal, in memory 44 and later, after a readout process is made available to the detector matrix of the periphery.

Figure 6:
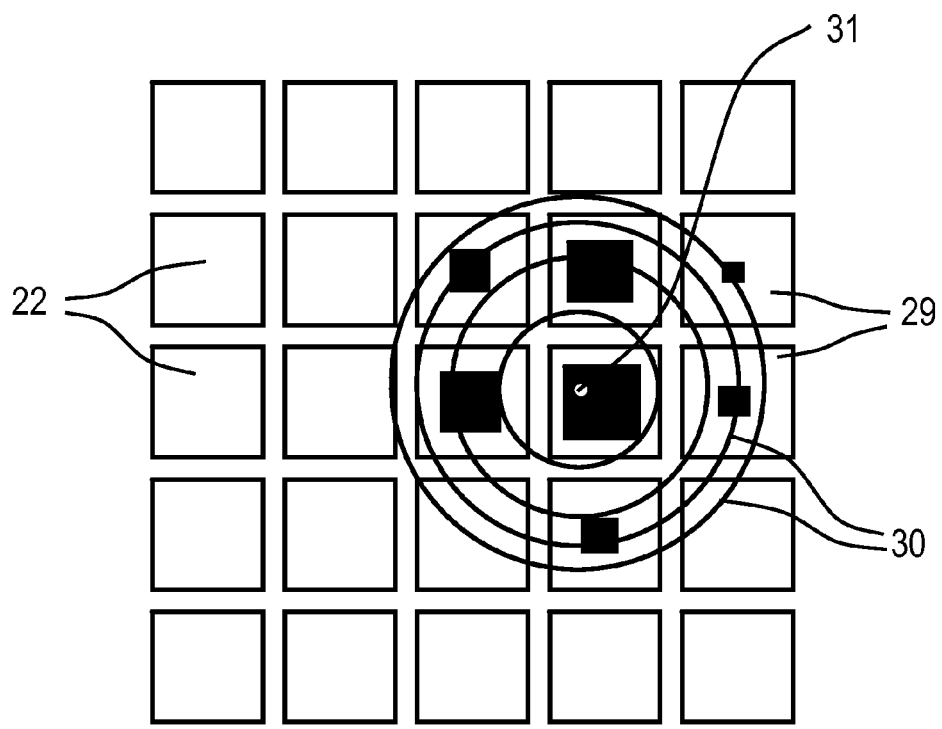
FIG. 6 shows the detector arrangement according to FIG. 5 with local determination of the interaction as a result of the signal distribution.

More complex variants of the location determination are for example two-dimensional fit function 30 to the local distribution of the pixel signals 26, as is indicated graphically in FIGS. 4 and 6.

FIGS. 3 and 4 reflect a schematic representation of how secondary quanta 25 of the primary event 24 (absorption of the x-ray quantum 23) are distributed over different detector pixels 22 and accordingly generate pixel signals 26 of different levels. From the location, e.g. a central pixel 32 or a node 35, the pixel signals 26 and their signal level, with the aid of a suitable function, e.g. the fit function 27, the maximum of the fit function 27 can be determined as virtual location 31, the accuracy of which is significantly higher than the rastering of the detector pixels 22. This virtual location 31 is the reconstructed location of the primary event 24, of the absorption of the x-ray quantum 23.

A two-dimensional representation of this state of affairs can be found in FIGS. 5 and 6, in which an x-ray quantum 23 strikes the conversion material of the detector layer 21, interacts and creates a number of pixel signals 26 in a number of neighboring detector pixels 29. In FIG. 6, on the basis of the signal distribution the location is determined by way of a suitable two-dimensional fit function 30 at which the x-ray quantum 23 has interacted with the conversion material.

A few examples of pixel-to-pixel connections 33 can be found in FIGS. 7 to 12. A central pixel 32 or a node 35 between the detector pixels 22 are connected to the direct horizontal and vertical and/or diagonal neighboring pixel 34. In the examples according to FIGS. 9 to 12, as well as the directly-neighboring pixels 34, there are additionally the next neighboring pixels 34.

FIG. 13 depicts a section from a resistance network only for the central pixel 32, from which, with a suitable choice of resistors 36 to 39 and those of the neighboring pixels 34, a significantly higher local resolution than the pixel resolution can be achieved.

FIGS. 14-15 illustrate a section from a pixel matrix, with connection of a central pixel 32 to its eight neighboring pixels 34. A precise location signal is computed by signal weighting from the digital pixel signals 26 of the central pixel 32 and its neighboring pixels 34, which is stored, together with the level of the overall signal, in memory 44.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Although the invention has been illustrated and described in detail on the basis of the preferred example embodiment, the invention is not limited by the disclosed examples and other variations can be derived herefrom by the person skilled in the art, without departing from the scope of protection of the invention.

What is claimed is:

1. An x-ray recording system for x-ray imaging of an object under examination via direct measurement of an interference pattern, the x-ray recording system comprising:
    at least one x-ray emitter configured to generate quasi-coherent x-ray radiation;
    an x-ray image detector; and
    a diffraction or phase grating between the object under examination and the x-ray image detector, the diffraction or phase gating configured to create an interference pattern in an nth Talbot order, the x-ray image detector configured to directly detect the interference pattern in the nth Talbot order, the x-ray image detector having a resolution of at least half the wavelength of the interference pattern in accordance with the Nyquist theory arising in the nth Talbot order.

2. The x-ray recording system of claim 1, wherein the x-ray recording system is configured to creates an absorption image, a differential phase-contrast (DPC) image or a dark field image.

3. The x-ray recording system of claim 2, wherein the at least one x-ray emitter is configured to create quasi-coherent x-ray radiation.

4. The x-ray recording system of claim 2, wherein the at least one x-ray emitter includes a plurality of field emission x-ray sources and is configured to create quasi-coherent x-ray radiation.

5. The x-ray recording system of claim 2, wherein the at least one x-ray emitter includes a microfocus source and is configured to create quasi-coherent x-ray radiation.

6. The x-ray recording system of claim 2, wherein the x-ray image detector comprises:
    a plurality of detector pixels in a matrix;
    a detector layer including a detector material, the detector layer configured to generate secondary quanta for each absorbed x-ray quantum and distribute the secondary quanta over at least two of the plurality of detector pixels in accordance with a modulation transfer function (MTF), the distributed secondary quanta being pixel signals of the at least two of the plurality of detector pixels, and
    wherein the x-ray recording system is configured to reconstruct a location of a primary event using the pixel signals.

7. The x-ray recording system of claim 1, wherein the at least one x-ray emitter is configured to create quasi-coherent x-ray radiation.

8. The x-ray recording system of claim 1, wherein the at least one x-ray emitter includes a plurality of field emission x-ray sources and is configured to create quasi-coherent x-ray radiation.

9. The x-ray recording system of claim 1, wherein the at least one x-ray emitter includes a microfocus source and is configured to create quasi-coherent x-ray radiation.

10. The x-ray recording system of claim 1, wherein the x-ray image detector comprises:
    a plurality of detector pixels in a matrix,
    a detector layer including a detector material, the detector layer configured to generate secondary quanta for each absorbed x-ray quantum and distribute the secondary quanta over at least two of the plurality of detector pixels in accordance with a modulation transfer function (MTF), the distributed secondary quanta being pixel signals of the at least two of the plurality of detector pixels, and
    the x-ray recording system is configured to reconstruct a location of a primary event using the pixel signals.

11. The x-ray recording system of claim 10, wherein the x-ray recording system is configured to determine the location of the primary event based on pixel signals in neighboring pixels of the at least two of the plurality of detector pixels.

12. The x-ray recording system of claim 11, wherein the x-ray recording system is configured to determine the location of the primary event using at least one of a fit function and a weighted averaging according to equation $(X, y)=\Sigma(x_i, y_i) \cdot S_i / \Sigma S_i$, wherein $(X, Y)$ is the computed location, $(x_i, y_i)$ and $S_i$ are measured pixel signals in the corresponding pixels i.

13. The x-ray recording system of claim 10, further comprising:
    a memory configured to store the location of each primary event.

14. The x-ray recording system of claim 1, wherein the x-ray image detector comprises:
    a plurality of detector pixels, the plurality of detector pixels being interconnected via pixel-to pixel connections.

15. The x-ray recording system of claim 1, wherein the x-ray image detector comprises:
    a plurality of detector pixels;
    a computation unit; and
    a memory, wherein the memory is configured to store signal levels of pixel signals of the plurality of detector pixels involved in primary events and a time stamp,
    wherein the computation unit is configured to reconstruct the primary event after the memory stores the signal levels.

16. The x-ray recording system of claim 1, wherein the x-ray detector comprises:
    a plurality of detector pixels; and
    a detector layer, wherein the detector layer includes a scintillator material configured to generate secondary quanta and distribute the secondary quanta over a number of detector pixels.

17. The x-ray recording system of claim 1, wherein the x-ray image detector is an integrating detector configured to indirectly convert x-ray quanta using Cesium Iodide (CsI), and the x-ray image detector includes a CMOS photodiode and readout structure.

18. The x-ray recording system of claim 1, wherein the x-ray image detector comprises a photon-counting detector configured to directly convert x-ray quanta.

* * * * *